"""

US008241618B2

(12) United States Patent
Brandt et al.

(10) Patent No.: US 8,241,618 B2
(45) Date of Patent: Aug. 14, 2012

(54) PROCESS FOR PRODUCING A HYDROPHOBICALLY MODIFIED POLYMER FOR USE WITH PERSONAL CARE COMPOSITIONS

(75) Inventors: Loralei Brandt, Campton Hills, IL (US); Jeffrey Cramm, Batavia, IL (US); Damyanti J. Patel, Hoffman Estates, IL (US); Yin Z. Hessefort, Naperville, IL (US); Wayne M. Carlson, Batavia, IL (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 386 days.

(21) Appl. No.: 12/543,953

(22) Filed: Aug. 19, 2009

(65) Prior Publication Data

US 2010/0008884 A1    Jan. 14, 2010

Related U.S. Application Data

(63) Continuation-in-part of application No. 11/044,383, filed on Jan. 27, 2005.

(51) Int. Cl.
*A61Q 5/02* (2006.01)
*A61Q 5/12* (2006.01)
*A61Q 19/00* (2006.01)
*A61K 8/81* (2006.01)
*C08L 33/26* (2006.01)
*C08F 220/56* (2006.01)

(52) U.S. Cl. .................. 424/70.17; 424/70.11; 510/130; 510/119; 510/276; 526/303.1; 526/304; 524/555

(58) Field of Classification Search ............... 424/70.17, 424/70.11; 510/130, 119, 276; 524/555; 526/303.1, 304
See application file for complete search history.

(56) References Cited

U.S. PATENT DOCUMENTS

| | | | |
|---|---|---|---|
| 2,438,091 A | 3/1948 | Lynch et al. | |
| 2,528,378 A | 10/1950 | Mannheimer et al. | |
| 2,658,072 A | 11/1953 | Kosmin et al. | |
| 4,401,650 A | 8/1983 | Salamone | |
| 4,680,339 A * | 7/1987 | Fong | 525/54.11 |
| 4,806,345 A | 2/1989 | Bhattacharyya | |
| 4,921,903 A * | 5/1990 | Fong | 524/555 |
| 4,970,290 A | 11/1990 | Fong | |
| 5,084,520 A | 1/1992 | Fong | |
| 5,089,578 A * | 2/1992 | Valint et al. | 526/240 |
| 5,573,709 A | 11/1996 | Wells | |
| 6,207,778 B1 | 3/2001 | Jachowicz et al. | |
| 6,410,005 B1 | 6/2002 | Galleguillos et al. | |
| 6,822,039 B1 * | 11/2004 | Monfreux-Gaillard et al. | 524/555 |
| 7,338,534 B2 * | 3/2008 | Kravtchenko et al. | 8/405 |
| 2004/0205902 A1 | 10/2004 | Cottard et al. | |
| 2007/0060488 A9 | 3/2007 | Samain et al. | |

FOREIGN PATENT DOCUMENTS

| | | |
|---|---|---|
| GB | EP 0 308 221 | 3/1989 |
| GB | 2260985 A | 5/1993 |
| WO | WO 02051367 A1 * | 7/2002 |
| WO | WO 2006081496 A2 * | 8/2006 |

OTHER PUBLICATIONS

Dallal, J., "Polyquaternium-55: A New Force in Styling Polymers", *Cosmetics and Toiletries Magazine* (C&T), vol. 117, No. 12, Dec. 2002, pp. 33-42.
Drovetskaya, T.V. et al: "Effects of Low-Level Hydrophobic Substitution on Conditioning Properties Cationic Cellulosic Polymers in Shampoo Systems", *Journal of Cosmetic Science, Society of Cosmetic Chemists*, New York, NY, US, vol. 55, No. Suppl. 2004, pp. 195-205.
Wu, Shuhui and Ra Shanks, "Synthesis and characterization of hydrophobic modified polyacrylamide", *Polymer International* 53:1821-1830 (2004).

* cited by examiner

*Primary Examiner* — Satya Sastri
(74) *Attorney, Agent, or Firm* — Christopher P. Demas

(57) ABSTRACT

A the process of producing a hydrophobically modified polymer that can be used as a cosmetically acceptable composition prepared by incorporating hydrophobic moieties into a polymer composed acrylamide, one or more cationic monomers and optionally one or more anionic monomers. The composition may be incorporated into products for treating hair, skin and nails and also into household products such as household cleaners and laundry detergents.

16 Claims, No Drawings

PROCESS FOR PRODUCING A HYDROPHOBICALLY MODIFIED POLYMER FOR USE WITH PERSONAL CARE COMPOSITIONS

CROSS REFERENCE TO RELATED APPLICATION

This application is a continuation-in-part of U.S. Ser. No. 11/044,383, filed Jan. 27, 2005, which is herein incorporated by reference.

TECHNICAL FIELD

This invention relates to the production of a cosmetically acceptable composition containing a polyacrylamide composed of acrylamide, one or more cationic monomer and optionally one or more anionic monomers where the polyacrylamide is modified by incorporation of hydrophobic groups and a method of using the composition for treating hair, skin and nails.

BACKGROUND OF THE INVENTION

Over the last twenty years, the personal care industry has expanded into the realm of hydrophobically modified polymers, mostly in the area of thickening. Such ingredients include modified hydroxethyl cellulose and acrylates/Beheneth-25 Methacrylate.

The rationale for making new polymers containing various alkyl groups is to introduce properties that may not be achieved through unmodified acrylate or acrylamide polymers alone. Despite the continual introduction of new polymeric products, the monomeric quaternaries, fatty amines and fatty alcohols and emollients continue to play a very important role in personal care products. Many products contain at least a small amount of these materials. However, these conditioning agents may build up on substrates such as hair over time, thereby decreasing the hair's volume. Therefore, there is an ongoing need for new products having properties which cannot be achieved by conventional polymers and which do not have the disadvantages associated with currently used monomeric materials.

SUMMARY OF THE INVENTION

This invention is a process of producing a cosmetically acceptable composition comprising one or more hydrophobically modified polyacrylamides wherein the polyacrylamide is composed acrylamide and one or more cationic monomers and optionally one or more anionic monomers.

The hydrophobically modified polyacrylamide enhances properties such as creaminess, slip, feel, viscosity and moisturization depending on the type of hydrophobic moiety incorporated into the polymer.

DETAILED DESCRIPTION OF THE INVENTION

"Anionic monomer" means a monomer as defined herein which possesses a net negative charge above a certain pH value. Representative anionic monomers include base addition salts of acrylic acid, methacrylic acid, itaconic acid, 2-acrylamido-2-methyl-1-propanesulfonic acid, sulfopropyl acrylate or methacrylate or other water-soluble forms of these or other polymerizable carboxylic or sulfonic acids, sulphomethylated acrylamide, allyl sulphonate, styrene sulfonic acid, sodium vinyl sulphonate, and the like. Preferred anionic monomers are acrylic acid and 2-acrylamido-2-methyl-1-propanesulfonic acid.

"Base addition salt" means the salt resulting from reaction of a carboxylic acid ($-CO_2H$) group with a suitable base such as the hydroxide, carbonate, or bicarbonate of a metal cation or tetraalkylammonium cation, or with ammonia, or an organic primary, secondary, or tertiary amine of sufficient basicity to form a salt with the carboxylic acid group. Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. Preferred base addition salts include the sodium and ammonium salts.

"Cationic monomer" means a vinylic monomer suitable for co-polymerization with acrylamide under free radical forming conditions and capable of maintaining a net positive charge after the transamidation reaction as described herein. Representative cationic monomers include, but are not limited to monomers having the following formulas.

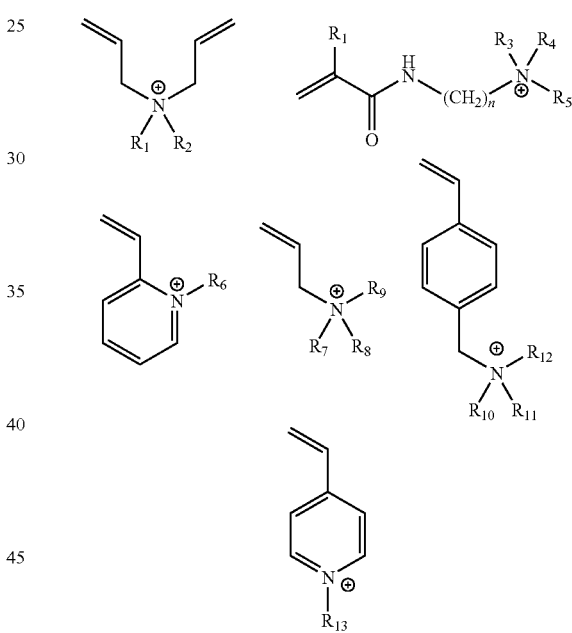

wherein $R_1$-$R_{13}$ are independently selected from H, $-CH_3$ and $-CH_2CH_3$ and n is 2 or 3.

"IV" stands for intrinsic viscosity, which is RSV extrapolated to the limit of infinite dilution, infinite dilution being when the concentration of polymer is equal to zero.

"Hydrophobic alkyl group" means an alkyl, alkenyl, cycloalkyl, aryl or arylalkyl group of about 4 to about 22 carbon atoms. Alkyl and alkenyl groups may be straight or branched and may be interrupted with one or more $-OSi(R')(R'')-$ and $-Si(R')(R'')-$ groups wherein R' and R'' are $C_1$-$C_4$ alkyl.

"Hydrophobic amine" means a compound containing at least one hydrophobic alkyl group and at least one amino hydrogen atom capable of undergoing a transamidation reaction with an amido ($-C(O)NH_2$) group of a polyacrylamide as defined herein to form a hydrophobically modified polyacrylamide. Hydrophobic amines containing $-OSi(R')(R'')-$ and $-Si(R')(R'')-$ groups are also referred to as "amino-functionalized silanes". Representative hydrophobic amines include benzylamine, cyclohexylamine, hexylamine, methylhexylamine, phenethylamine, octylamine, oleylamine, decylamine, dodecylamine, octadecylamine, and the like.

Representative amino-functionalized silanes include amines of formula

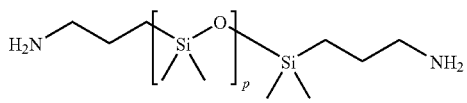

wherein p is about 5 to about 500, available from Aldrich, Milwaukee, Wis.; aminoethylpropyl silicone compounds available from Noveon, Cleveland, Ohio under the tradename Ultrasil and from Siltech Corporation, Toronto, Ontario, Canada under the tradename Silamine; and amine functional silicones including Dow Corning® 8220, Dow Corning® 939, Dow Corning® 949, Dow Corning® 2-8194, all available from Dow Corning, Midland, Mich., and Silicone SM 253 available from General Electric, Waterford, N.Y.

"Hydrophobically modified polymer" and "hydrophobically modified polyacrylamide" mean a polyacrylamide as defined herein wherein a portion of the amido (—C(O)NH$_2$) groups along the polymer backbone is modified by transamidation with a hydrophobic amine. Accordingly, in addition to repeating units derived from cationic monomers and any anionic monomers the hydrophobically modified polymer comprises repeating units having the following structures where NRaRb represents the hydrophobic group resulting from transamidation with a hydrophobic amine and M is H or a base addition salt.

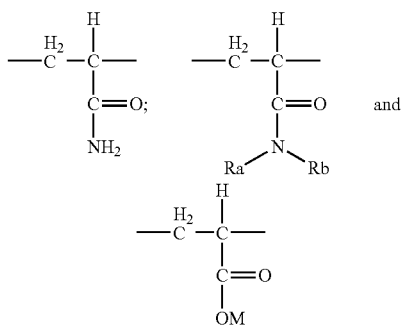

"Polyacrylamide" means a polymer formed by polymerization of acrylamide, one or more cationic monomers and any anionic monomers as defined herein under free radical forming conditions. Suitable polyacrylamides are commercially available in emulsion, dispersion, solution and powder form or can be prepared by standard methods used for free radical polymerization of vinyl monomers.

"RSV" stands for Reduced Specific Viscosity. Within a series of polymer homologs which are substantially linear and well solvated, "reduced specific viscosity (RSV)" measurements for dilute polymer solutions are an indication of polymer chain length and average molecular weight according to Paul J. Flory, in "Principles of Polymer Chemistry", Cornell University Press, Ithaca, N.Y., ©1953, Chapter VII, "Determination of Molecular Weights", pp. 266-316. The RSV is measured at a given polymer concentration and temperature and calculated as follows:

$$RSV = \frac{[(\eta/\eta_o) - 1]}{c}$$

$\eta$=viscosity of polymer solution
$\eta_o$=viscosity of solvent at the same temperature
c=concentration of polymer in solution.

The units of concentration "c" are (grams/100 ml or g/deciliter). Therefore, the units of RSV are dL/g. In this patent application, a 1.0 molar sodium chloride solution is used for measuring RSV, unless specified. The polymer concentration in this solvent is 0.100 g/dL. The RSV is measured at 30° C. The viscosities $\eta$ and $\eta_o$ are measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dL/g. When two polymer homologs within a series have similar RSV's that is an indication that they have similar molecular weights.

"Cosmetically acceptable excipient" means a non-toxic, non-irritating substance which when mixed with the hydrophobically modified polymer of this invention makes the polymer more suitable to be applied to hair or skin.

In an embodiment, the hydrophobically modified polymer of this invention is prepared by transamidation of amido (—C(O)NH$_2$) groups of a cationic polyacrylamide with about 0.1 about 10 mole percent of one or more hydrophobic amines by heating at elevated temperature and pressure. Base may be added to maintain the hydrophobic amine in its basic rather than protonated form. Suitable bases include ammonia and alkali and alkaline earth metal hydroxides and carbonates.

In an embodiment, the cationic polyacrylamide is mixed with an aqueous sulfite solution made from sodium metabisulfite and sodium hydroxide in a stainless steel pressure reactor at a pH of about 5-11 preferable 8-10. The hydrophobic amine is added, and the air in the reactor is replaced with nitrogen. The mixture is heated at about 120 to about 180° C. for about 0.5 to about 8 hours. In an embodiment, the mixture is heated at about 140° C. for about 5 hours. The resulting hydrophobically modified polymer is then diluted to the desired concentration with water and optionally treated with one or more preservatives at elevated temperature. In an embodiment, the hydrophobically modified polymer solution is treated with methyl paraben and propyl paraben at 85-90° C. for 1 hour. The product is characterized by viscometric, $^{13}$C NMR, GC, and GPC methods.

In an embodiment, the cationic polyacrylamide is composed of at least about 30 mole percent preferable 50 mole percent acrylamide.

In an embodiment, the hydrophobically modified polymer has a RSV of about 0.1 to about 8 dL/g.

In an embodiment, the cationic monomers are selected from diallyldimethylammonium chloride and methacrylamidopropyltrimethylammonium chloride.

In an embodiment, the hydrophobic amines are selected from the group consisting of $C_6$-$C_{22}$ alkyl amines and amino functionalized silicones.

In an embodiment, the hydrophobically modified polymer has a RSV of about 1 to about 5.

In an embodiment, the cationic polyacrylamide is acrylamide/diallyldimethylammonium chloride copolymer.

In an embodiment, the cationic polyacrylamide is acrylamide/diallyldimethylammonium chloride/acrylic acid terpolymer.

In an embodiment, the alkyl amines are selected from the group consisting of octylamine, dodecylamine and hexadecylamine.

In an embodiment, the composition further comprises one or more cosmetically acceptable excipients.

In an embodiment, the cosmetically acceptable composition comprises about 0.01 to about 40 weight percent, based on polymer solids, of hydrophobically modified polymer.

In an embodiment, the cosmetically acceptable excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid (poly-N acetyl-neuraminic acid), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, starch hydroxypropyltrimoium chloride, hydroxyproyl starch phosphate, steardimonium hydroxyethyl cellulose, raffinose, rhamsan, tapioca starch, whelan, levan, scieroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, N.Y. pp. 578-611 (1994) which is incorporated entirely by reference. Complex carbohydrates can be found in Kirk-Othmer *Encyclopedia of Chemical Technology*, Fourth Edition, Vol. 4, John Wiley and Sons, NY pp. 930-948, 1995 which is herein incorporated by reference.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents.

Anionic surface-active agents useful herein include those disclosed in U.S. Pat. No. 5,573,709, incorporated herein by reference. Examples include alkyl and alkyl ether sulfates.

Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof. The structure or representative quaternary ammonium compounds is provided in the CTFA Cosmetic Ingredient Handbook, Fifth Edition, 1988, page 40.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowdimonium chloride, hydroxycetyl hydroxyethyl dimonium chloride, hydroxyethyl behenamidopropyl dimonium chloride, hydroxyethyl cetyldimonium chloride, hydroxyethyl tallowdimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, polyquaternium-55, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine.

The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used, the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning®, Midland, Mich., USA. Additional alkyl and phenyl silicones may be employed to enhance moisturizing properties. Resins such as dimethicone (and) trimethylsiloxysilicate, known as Dow Corning® 593 or cyclomethicone (and) trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the tradename Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile silicones can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the tradenames Dow Corning® 244 fluid, Dow Corning® 245 fluid, Dow Corning® 246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises about $C_6$ to $C_{22}$ atoms. A preferred volatile hydrocarbon is an aliphatic hydrocarbon having a chain length of about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17th Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, Polyquaternium-55 and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10-30 Alkyl Acrylate Crosspolymer, such as the Carbopol® and Pemulen® series, both available from Noveon, Inc., Cleveland, Ohio, USA; anionic acrylate polymers such as Salcare® AST and cationic acrylate polymers such as Salcare® SC96, available from Ciba Specialties, High Point, N.C., USA; acrylamidopropyltrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28, available from Rohm and Haas/International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl)aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Examples of preservatives include, but are not limited to, 1,2-dibromo-2,4-dicyano butane (Methyldibromo Glutaronitrile, known as MERGUARD®, Ondeo Nalco Company, Naperville, Ill., USA), benzyl alcohol, imidazolidinyl urea, 1,3-bis (hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to, buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the anionic polymer described herein and then used in the cosmetically acceptable composition of this invention. The treated pigments are then more effective as sunscreen actives and for use in color cosmetics such as make up and mascara.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include aftershaves, sunscreens, lotions, hand and body creams, liquid soaps, bar soaps, bath oil bars, shaving creams, dishwashing liquids, shower gels, bubble baths, and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The hydrophobically modified polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the hydrophobically modified polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-53), guar hydroxypropyl trimonium chloride, starch hydroxypropyl trimonium chloride and polymethacrylamidopropyl yrimonium chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylic acid thickeners available from B.F. Goodrich; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given hydrophobically modified polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylatelvinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

If the compositions of the instant invention are intended for use in the dyeing of keratin fibers, and in particular human hair, they generally contain at least one oxidation dyestuff precursor and/or one direct dyestuff, in addition to the hydrophobically modified polymer. They also can contain any other adjuvant normally used in this type of composition.

The pH of the dyeing compositions is generally 7 to 11 and can be adjusted to the desired value by adding an alkalizing agent.

The compositions according to this invention also can be used for waving or straightening the hair. In this case, the composition generally contains, in addition to the hydrophobically modified polymer, one or more reducing agents and, if appropriate, other adjuvants normally used in this type of composition; such compositions are intended for use conjointly with a neutralizing composition.

In an embodiment, this invention is a method of treating a substrate selected from hair, skin and nails comprising applying to the substrate a cosmetically acceptable composition comprising one or more hydrophobically modified polyacrylamides wherein the polyacrylamide is composed acrylamide and one or more cationic monomers.

In another embodiment, the substrate is hair.

In another embodiment, this invention is a household cleaner or laundry detergent comprising one or more hydrophobically modified polyacrylamides wherein the polyacrylamide is composed of acrylamide, one or more cationic monomers and optionally one or more anionic monomers.

The foregoing may be better understood by reference to the following examples, which are presented for purposes of illustration and are not intended to limit the scope of this invention.

Example 1

Modification of Acrylamide-diallyldimethylammonium Chloride Copolymer with Hexadecylamine.

To a Parr reactor is added an aqueous solution of acrylamide-diallyldimethylammonium chloride copolymer solution (69.5:30.5 mole percent, 20 percent polymer actives, 225 g), a mixture of aqueous sodium hydroxide solution (50%, 2.3 g) and aqueous sodium metabisulfite solution (15%, 19.2 g) and deionized water (200 g). Finely ground hexadecylamine is then added and the mixture is thoroughly stirred. The reactor is then sealed, the stirring is set to the maximum setting and the reactor is pressurized with nitrogen and vented (repeat five times). The reactor is then sealed, heated to 140° C. and maintained at 140° C. for five hours. Heating is then stopped and the reactor is allowed to cool to ambient temperature to provide an aqueous solution of hydrophobically modified polymer. The properties of representative hydrophobically modified polymers is shown in Table 1. In Table 1, AcAm stands for acrylamide, DADMAC for diallyldimethylammonium chloride and MAPTAC for methacrylamidopropyltrimethylammonium chloride.

TABLE 1

| Polymer | Unmodified polymer monomer content (mole %) | | | Modifier (mole %) | Unmodified Polymer RSV (dL/g) | Modified polymer solution conc. | Modified Polymer RSV (dL/g) |
| --- | --- | --- | --- | --- | --- | --- | --- |
| | AcAm | DADMAC | MAPTAC | | | | |
| I | 69.5 | 30.5 | — | Hexadecyl amine (3) | 1.2 | 12 | 1.1 |
| II | 69.5 | 30.5 | — | Dodecyl amine (0.5) | 1.2 | 8 | 1.8 |
| III | 69.5 | 30.5 | — | Octyl amine (3) | 1.2 | 8 | 1.7 |
| IV | 69.5 | 30.5 | — | Dodecyl amine (1) | 3.2 | 5 | 3.2 |
| V | 50 | — | 50 | Dodecyl amine (0.6) | 3.7 | 19 | 3.7 |
| VI | 80 | — | 20 | Dodecyl amine (0.75) | 5.3 | 8 | 4.9 |
| VII | 80 | — | 20 | Hexadecyl amine (1.0) | 5.3 | 8 | 4.9 |
| VIII | 80 | — | 20 | Octyl amine (10) | 5.3 | 8 | 3.5 |
| IX | 69.5 | 30.5 | — | Amino-functionalized silicone[1] (0.3) | 1.4 | 8 | 1.6 |
| X | 69.5 | 30.5 | — | Amino-functionalized silicone[2] (0.3) | 1.4 | 8 | 1.6 |

[1] Amino-functionalized silicone of formula $H_2N(CH_2)_3[Si(CH_3)_2O]_pSi(CH_3)_2(CH_2)_3NH_2$ wherein p is about 50, Aldrich, Milwaukee, WI.
[2] Ultrasil ™ A-23, Noveon, Cleveland, OH.

Example 2

Preparation of a Hydrophobically Modified Polymer Solution.

The aqueous polymer solution of Example 1 (445 g) is transferred to a flask and heated to 85° C. with stirring. A mixture of methyl paraben (0.6 g), propyl paraben (0.12 g) and deionized water (30 g) is heated to dissolve the parabens and then added to the hot polymer solution. The mixture is stirred at 85° C. for one hour and then cooled to ambient temperature to provide the hydrophobically modified polymer solution.

In the following examples, "C8 Polymer" means a 69.5 mole percent acrylamide/30.5 mole percent diallyldimethylammonium chloride copolymer modified with octylamine. "C12 Polymer" means a 69.5 mole percent acrylamide/30.5 mole percent diallyldimethylammonium chloride copolymer modified with dodecylamine. "C16 Polymer" means a 69.5 mole percent acrylamide/30.5 mole percent diallyldimethylammonium chloride copolymer modified with hexadecylamine.

Example 3

Preparation of a Representative Shampoo.

The components shown in Table 2 are added in the order listed with complete mixing after each addition. The batch is heated to 55° C. to 65° C. to melt cocamide MIPA and the batch pH is adjusted to 5.5 to 6.5 with lactic acid. The preservatives are added at a temperature less than about 40° C. The polymer is diluted with water to result in a total batch of about 200 g and the mixture is stirred for about 15 minutes. The shampoo is degassed to remove any entrapped air prior to viscosity measurements.

TABLE 2

Base Shampoo Formulation

| Ingredient | C-8 modified polymer Weight % | C-12 modified polymer Weight % |
|---|---|---|
| DI Water | 50.166 | 48.166 |
| Ammonium Lauryl Sulfate, 28% | 20.00 | 20.00 |
| Sodium Lauryl Sulfate, 29% | 20.00 | 20.00 |
| Cocamidopropyl Betaine, 30% | 3.00 | 3.00 |
| Cocamide MIPA (s) | 3.00 | 3.00 |
| C8 Polymer, 8% | 3.125 | 0.00 |
| C12 Polymer, 5% | 0.00 | 5.00 |
| Lactic Acid | 0.059 | 0.059 |
| Sodium Chloride | 0.300 | 0.300 |
| Disodium EDTA | 0.10 | 0.10 |
| Kathon CG | 0.05 | 0.05 |
| DMDM Hydantoin | 0.10 | 0.10 |
| Fragrance | 0.10 | 0.10 |

Example 4

Evaluation of Base Shampoo Containing Different Levels of Hydrophobically Modified Polymer.

Representative shampoo formulations prepared according to the method of Example 3 are tested for foam stability and viscosity. Viscosity measurements are obtained using a Brookfield DV-I+Viscometer (Middleboro, Mass.). The results are illustrated in the Table 3. It is clear that the representative polymer shows synergetic effect of viscosity with shampoo system. The viscosity plays a relatively important role in hair care product since thick in viscosity can be perceived by consumer as luxuries or richness. The shampoos with and without polymer are also tested for foaming property. Polymer, especially conditioning polymer, usually has an adverse effect on the foaming property to the shampoo. The addition of representative polymer in the shampoo increases the foaming time for almost 3 times.

TABLE 3

Evaluation of Base Shampoo Containing Different Levels of Hydrophobically Modified Polymer

| Sample | Viscosity 5/20 (cps) | | | Lather | | |
|---|---|---|---|---|---|---|
| Level of Polymer | 0.25% | 0.5% | 1.0% | 0.25% | 0.5% | 1.0% |
| Control Shampoo | 11,220 | 12,880 | 9850 | Creamy | Creamy | Creamy |
| 1 mole C12 polymer | 14,100 | 15,340 | 17,620 | Creamier | Creamier | Creamier |
| 0.40 mole C12 polymer | 15,240 | 17,360 | 23,800 | Creamier | Creamier | Creamier |

Example 5

Preparation of a Natural Shampoo Formulation.

A natural shampoo formulation is prepared using the ingredients shown in Table 4.

TABLE 4

Natural Shampoo Formulation

| Composition Ingredient | INCI Name | Weight % |
|---|---|---|
| Deionized Water | Water | QS |
| Geropon SBFA-30 | Disodium Laureth-3 Sulfosuccinate | 3.00 |
| Standapol A | Ammonium Lauryl Sulfate, 30% | 30.00 |
| Plantacare 818UP | Coco-glucoside | 3.00 |
| Glucamate DOE-120 | PEG-120 Methyl Glucose Dioleate | 2.10 |
| Velvetex AB-45 | Coco-Betaine | 8.00 |
| Methyl Paraben | Methyl Paraben | 0.20 |
| Propyl Paraben | Propyl Paraben | 0.10 |
| Tween 20 | Polysorbate 20 | 0.00 |
| Polymer | Polymer | 0.25 |
| Citric Acid, 50% | Citric Acid, 50% | QS |

Example 6

Evaluation of a Natural Shampoo Containing a Representative Hydrophobically Modified Polymer.

A natural shampoo formulation prepared as described in Example 5 is evaluated for viscosity, lather rinse off time and slip. The shampoo is slightly sticky due to glucose/ethoxyate. The results are shown in Table 5. The formulation is improved by the addition of hydrophobically modified polymer that reduced the sticky feel from the control base. Overall, the hydrophobically modified polymer added to shampoo makes the foam feel slightly creamier than the control without polymer.

TABLE 5

Evaluation of Natural Shampoo Containing Hydrophobically Modified Polymer

| Sample | Viscosity 5/20 (cps) | Visual Observation | Lather | Rinse off Time (sec) | Slip |
|---|---|---|---|---|---|
| Control Natural Shampoo | 9,360 | Clear | Creamy | 1-2 (sticky) | 4 |
| 0.5 mole C16 polymer | 11,080 | Clear | Creamy | 2 | 4 |

Example 7

Evaluation of a Commercial Shampoo Containing a Representative Hydrophobically Modified Polymer.

Representative polymers of this invention modified with $C_8$ and $C_{12}$ alkyl groups (0.25 weight percent) are placed into Suave® Shampoo to confirm that samples remain clear. Suave Natural Strawberry shampoo is also investigated to prove the principle that hydrophobically modified polymers may be post-added to existing formulations. Typically, conditioning polymer added to these systems produces haziness. The $C_8$ and $C_{12}$ polymers added to these systems maintain better clarity and added slip and creaminess to the formulation. After three months, the Suave® Mountain Strawberry shampoo base remain clear with the $C_8$ and $C_{12}$ polymer. Polyquaternium-7, an example of a typical conditioning polymer, post-added to this formulation remains cloudy. The introduction of the hydrophobically modified polymer serves to increase the potential surfactant compatibility with the ALS/ALES surfactant system of the Suave shampoo base.

Example 8

Evaluation of Foaming Properties of Shampoo Containing a Representative Hydrophobically Modified Polymer.

A representative shampoo composition prepared using a polymer modified with a C12 alkyl group having the ingredients shown in Table 6 is prepared and evaluated in the Hart de George Foam Test. The test results show that hydrophobically modified polymer creates more stable shampoo foams and therefore a longer drain time (23 seconds for a shampoo formulation prepared with a polymer modified with a C12 hydrophobic group compared to 8.3 seconds for a shampoo formulation prepared with unmodified polymer).

TABLE 6

Shampoo Formulation Used in Hart de George Foam Test

| Ingredient | Weight % |
|---|---|
| DI Water | 48.266 |
| Sodium Lauryl Sulfate, 29% | 10.00 |
| Sodium Lauryl Ether Sulfate, 28% | 30.00 |
| Cocamidopropyl Betaine, 30% | 3.00 |
| Cocamide MIPA (s) | 1.00 |
| C12 Polymer | 5.00 |
| Citric Acid, 100% (s) | |
| Sodium Chloride | |
| Disodium EDTA | 0.10 |
| Methylchloroisothiazolinone Methylisothiazolinone | 0.05 |
| DMDM Hydantoin | 0.10 |

Example 9

Instrumental Wet Combing Evaluation of Hydrophobically Modified Polymer.

Wet combing is a typical testing method used to illustrate the conditioning property of substances brought to hair care formulations. The hair tress is treated with 0.5% active solution and then rinsed. The treated hair tress is then tested in DiaStron Tensile Tester (MITT160, Hampshire, UK) for combing force. The lower amount of combing force needed in the test means the hair tress is well conditioned. The following Tables 7 and 8 indicate that the hair tresses treated with representative polymers have superior combing properties.

TABLE 7

Statistic Values for Combing Analysis

| Level | Number | Mean | Std Error | Lower 95% | Upper 95% |
|---|---|---|---|---|---|
| C-8 Polymer | 4 | 215.000 | 79.174 | 21.27 | 408.73 |
| Control | 4 | 551.250 | 79.174 | 357.52 | 744.98 |

TABLE 8

Statistic Values for Combing Analysis

| Level | Number | Mean | Std Error | Lower 95% | Upper 95% |
|---|---|---|---|---|---|
| C-12 polymer | 6 | 64.117 | 33.822 | −11.2 | 139.48 |
| Control | 6 | 512.333 | 33.822 | 437.0 | 587.69 |

Example 10

Evaluation of Sensory Wet Combing and Lubricity Properties in a Conditioner Formulation.

A conditioning formulation containing the ingredients shown in Table 9 is prepared as follows.

Hydroxyethylcellulose (HEC) is sprinkled into water and mixed at moderate speed for 30 minutes. The solution is heated to 40° C. to ensure that the solution is clear and homogeneous. Stearamidopropyldimethylamine is then added, the pH is adjusted to 4.0 with citric acid and the dicetyldimonium chloride is added. The thickened mixture is heated to 70° C. and a blend of cetyl, stearyl and Promulgen G (and behenyl) is added. The mixture is heated to 80-85° C. and held for thirty minutes. Cooling is then initiated and cold deionized water is added slowly. The mixture is allowed to mix and cool and the silicone blend is added at a temperature below 55° C. EDTA 0.05/30 dilution is added slowly at a temperature below 40° C. and the preservatives are finally added at a temperature below 35° C.

TABLE 9

Conditioning Formulation

| Ingredients | PEG-2/DCQ 1% C16 Composition | PEG-2/DCQ 1% C8 |
|---|---|---|
| Deionized Water | 45.00 | 45.00 |
| Hydroxyethylcellulose (HEC) | 0.20 | 0.20 |
| Citric Acid, 50% | 0.12 | 0.12 |
| Stearamidopropyl Dimethylamine | 0.50 | 0.50 |
| Dicetyldimonium chloride, 67% | 2.00 | 1.50 |
| PEG-2 Oleamonium chloride, 69% | 0.50 | 0.50 |
| Behentrimonium Methosulfate (50%) and Cetyl Alcohol and 1,3 butanediol | 0.00 | 0.00 |
| Cetyl Alcohol (C95) | 3.00 | 3.00 |
| Stearyl Alcohol (S95) | 2.00 | 2.00 |
| Stearyl Alcohol (70%) and Ceteareth-20 (30%) | 1.00 | 1.00 |
| Silicone | 0.50 | 0.00 |
| Deinionized water cooling to 50-55 C. | 21.03 | 21.93 |
| Disodium EDTA | 0.05 | 0.05 |
| Deinionized water | 2.90 | 3.00 |
| DBDCB (and) Dipropylene Glycol | 0.10 | 0.10 |
| DMDM Hydantoin | 0.10 | 0.10 |
| Deionized water* (dilute polymer with DI) | 20.00 | 20.00 |
| Ddeionized water | 0.00 | 0.00 |
| C16 Polymer | 1.00 | 0.00 |
| C8 Polymer | 0.00 | 1.00 |

Example 11

Evaluation of Sensory Wet Combing and Lubricity Properties in a Conditioner Formulation.

The wet detangling wet combing and lubricity panel tests are conducted to assess conditioner formulations prepared as in Example 10 as follows.

1. Trained evaluators able to reliably differentiate between damaged and treated hair tresses perform the tests.
2. The tests are carried out with a total of three replicates per panel.
3. For each test, an untreated dark-bleached tress and a conditioner treated tress serve as references.
4. Each tress is treated with 1 ml of product and massaged into the tress for 60 seconds, followed by rinsing under 38° C. tap water for 30 seconds.
5. Tresses are detangled and the panel is set up. Each tress is dipped three times in 500 ml of deionized water to reintroduce tangles. The excess water is then removed using a gloved hand.
6. Panelists use the wide end of the black plastic Sally comb to detangle two times.
7. Next, panelists utilize the small tooth portion to wet comb the tresses twice.
8. The lubricity is evaluated by combing the tress by a down and up cycle four times to evaluate interfiber friction.
9. After each test, tresses are dipped three times in deionized water to reintroduce tangles and excess water removed with a gloved hand.

Five panelists typically rate the tresses (1=high friction to 5=low friction). The results are shown in Table 10-12. Higher detangling wet combing and lubricity numbers are indicative of better performance.

TABLE 10

Wet Detangling and Combing of C16 Hydrophobically Modified Polymer Containing Conditioner

| Composition | Wet Detangle | Wet Comb | Lubricity |
|---|---|---|---|
| Untreated | 1.94 | 1.56 | 1.49 |
| C16 Polymer | 4.07 | 3.73 | 3.57 |

TABLE 11

Wet Detangling and Combing of C8 Hydrophobe in Conditioner

| Composition | Wet Detangle | Wet Comb | Lubricity |
|---|---|---|---|
| Untreated | 2.13 | 1.71 | 1.50 |
| C8 Polymer | 4.26 | 3.96 | 3.79 |

TABLE 12

Wet Detangling and Combing of C12 Hydrophobe in Conditioner

| Composition | Wet Detangle | Wet Comb | Lubricity |
|---|---|---|---|
| Untreated | 2.29 | 2.04 | 1.63 |
| C12 Polymer | 3.67 | 3.37 | 3.27 |

As shown in Tables 10-12, hydrophobically modified polymers of the present invention provide excellent wet properties significantly better than the untreated dark bleached hair.

Example 12

Evaluation of Smoothness and Film Evaluation of Moisturizing Smoothie Gel.

Smoothness and film evaluation of a smoothie gel formulation according to Table 13 is conducted using a panel test as follows.

TABLE 13

Moisturizing Smoothie Gel

| Ingredient | Control Weight % | C8-Polymer Weight % | C-12 Polymer Weight % | Polyquaternium-7 Weight % |
|---|---|---|---|---|
| Water | Qs | Qs | qs | qs |
| Hydroxyethylcellulose | 0.53 | 0.53 | 0.53 | 0.53 |
| Polyquaternium-4 | 0.17 | 0.17 | 0.17 | 0.17 |
| C8 Polymer (8%) | 0.00 | 4.00 | 0.00 | 0.00 |
| C12 Polymer (5%) | 0.00 | 0.00 | 4.00 | 0.00 |
| Polyquaternium-7 | 0.00 | 0.00 | 0.00 | 4.00 |
| Meadowfoam Seed Oil | 0.025 | 0.025 | 0.025 | 0.025 |
| DMDM Hydantoin | 0.20 | 0.20 | 0.20 | 0.20 |
| Fragrance | 0.10 | 0.10 | 0.10 | 0.10 |
| Oleth-20 | 0.20 | 0.20 | 0.20 | 0.20 |

Panel test of smooth feel and film.

1. Prepare a one gram sample, six inches in length each of virgin hair (International Hair Importers, Bellerose, N.Y., USA).
2. Apply one gram of polymer onto tresses. Tresses are stroked 25 times to ensure coverage.
3. Comb each tress with the wide end of the Sally styling comb to detangle.
4. Allow samples to air dry.

5. Randomized panelists run their fingers from top to bottom of the hair tresses and rate tresses according to intensity (1=not smooth to 5=very smooth) and film stiffness (1=not stiff to 5=very stiff).

Slippery feel can aid the aesthetics of a product and allow hair fibers to slide past one another. This is an important goal of any conditioning product. A panel evaluated the slippery and smooth feel of the formulations from the formulation above using the following protocol. The results are tabulated in Table 14.

TABLE 14

Table Panel Assessment of Moisturizing Smoothie Gel

| Formulation | Smooth Feel (n = 4) | Film Stiffness (n = 4) |
|---|---|---|
| Water | 4.0 | 1.0 |
| Polyquaternium-7 | 2.9 | 3.6 |
| Control Formulation | 2.8 | 4.3 |
| C8 Polymer | 3.0 | 4.8 |
| C16 Polymer | 3.1 | 4.8 |

As shown in the table 14 hydrophobically modified polymers of this invention show improved stiffness and slightly improved smoothness over the control formula.

Examples 13-16

Representative Hair Care Formulations Containing Hydrophobically Modified Polymers are Formulated as Shown in Examples 13-16.

TABLE 15

Moisturizing Shampoo

| Ingredient | Weight % |
|---|---|
| DI Water | 49.11 |
| Sodium Lauryl Sulfate, 29% | 20.00 |
| Sodium Lauryl Ether Sulfate, 28% | 20.00 |
| Cocamidopropyl Betaine, 30% | 3.00 |
| Lauramide DEA | 3.00 |
| Fatty Acid/PG-2 | 0.50 |
| C8 Polymer | 3.13 |
| Citric Acid, 100% (s) | 0.60 |
| Sodium Chloride | 1.36 |
| Disodium EDTA | 0.10 |
| DMDM Hydantoin | 0.10 |
| Yellow | 0.038 |
| Green | 0.041 |

Viscosity is 13480 cps at spindle/speed 5/20 after 30 seconds. The shampoo gives very creamy foam.

Example 14

Less Volume Leave in Conditioner.

TABLE 16

Less-Volume Leave-in Conditioner

| Composition Ingredient | Weight % | Weight % |
|---|---|---|
| Water | | |
| Hydroxyethyl cellulose | 1.00 | 1.00 |
| Dicetyldimonium•Cl (Varisoft 432CG) | 3.00 | 3.00 |
| Amodimethicone (and) Cetrimonium chloride (and) Nonoxynol-10 (DC 949) | 0.25 | 0.25 |
| C8 Polymer, 8% | 12.50 | 0.00 |
| Apple Herbal Fragrance | 0.10 | 0.10 |
| DMDM Hydantoin | 0.40 | 0.20 |

The effect of a C8 hydrophobically modified polymer on the hair is to provide smoothness, gloss and straighten the hair when used in this formula. Hair is more effectively straightened and smoothed when using 1% active polymer versus control formulation without polymer.

Example 15

Ethnic Conditioner.

TABLE 17

Ethnic Conditioner

| Composition Ingredient | Weight % | Weight % |
|---|---|---|
| Water, Deionized | qs | Qs |
| Hydroxyethyl cellulose | 0.30 | 0.30 |
| Stearamidopropyldimethylamine | 0.50 | 0.50 |
| Dicetyldimonium•Cl (Varisoft 432CG) | 3.00 | 3.00 |
| Cetyl Alcohol | 5.00 | 5.00 |
| Stearyl Alcohol and Ceteareth-20 | 2.00 | 2.00 |
| Citric acid, 50% | qs | Qs |
| C8 Polymer | 3.00 | 0.00 |
| C16 Polymer | 0.00 | 3.00 |
| Cyclomethicone | 1.00 | 1.00 |
| Dimethicone 10CS | 0.20 | 0.20 |
| DMDM Hydantoin | 0.20 | 0.20 |

This ethnic conditioner gives excellent spreading and coverage of the hair shaft.

Example 16

Hair Lotion.

A hair lotion is created to smooth the hair.

TABLE 16

Hair Lotion

| Ingredient | Weight % | Weight % |
|---|---|---|
| Water, Deionized | qs | qs |
| Cocamidopropylbetaine | 2.00 | 2.00 |
| Hydroxyethyl cellulose | 0.50 | 0.50 |
| Acrylamide/DADMAC/Acrylic Acid polymer | 2.00 | 2.00 |
| C8 Polymer | 5.00 | 0.00 |
| C12 Polymer | 0.00 | 5.00 |
| PEG-40 Hydropgenated Castor Oil | 0.20 | 0.20 |
| Fragrance | 0.10 | 0.10 |
| DMDM Hydantoin | 0.20 | 0.20 |

Example 17

Evaluation of Hydrophobically Modified Polymer in Hair Styling Applications.

Representative formulations containing hydrophobically modified polymers are tested for curl retention, an evaluation tool for styling applications.

Six inch long, bleached, and pretabbed hair tresses are available from International Hair Importes and Products Inc.

Six inch long, bleached, and hand made hair tresses are available from DeMeo Brothers Inc.

The tresses are prepared for testing by cutting ⅛" width of hair from the pretabbed hair tress (0.4 g for each tress). The hair tress is wetted with water and then 0.3 g of sodium laureth sulfate is massaged onto the hair tress from top to bottom for 1 minute. The hair tress is then rinsed under 40±2° C. tap water for 1 minute. The washed hair tresses are soaked in deionized water overnight.

Clean hair tresses are immersed in a 0.5 weight percent aqueous polymer solution for 2 minutes. The excess solution is squeezed from the tress with gloved fingers. Each tress is combed to detangle with the wide end of Sally Styling Combs, then the hair is rolled onto a roller (1¹/₁₆" in diameter). The hair rolls are placed in a 50% relative humidity room overnight. The next day, the hair is unwound from each roller and the curled hair is placed in a 90% relative humidity chamber. The length of the curl (fall-out) is measured every 15 minutes for 2 hours and curl retention is calculated by the following equation:

Curl Retention Calculation $$\% \text{ Curl Retention} = \frac{(L - Lt)}{(L - Lo)} \times 100 \quad \text{Equation 1}$$

Where L=Length of hair tress fully extended

Lo=Length of hair tress at beginning of experiment

Lt=length of hair tress at time of measurement

The following table illustrates the curl retention of C-16 polymer against benchmark (Methacrylic acid/sodium acrylamidomethyl propane sulfonate copolymer)

TABLE 19

Curl Retention

| Time | Control | C-16, Polymer | Benchmark |
|---|---|---|---|
| 15 | 51.10 | 78.24 | 85.32 |
| 30 | 38.05 | 68.00 | 75.30 |
| 45 | 33.41 | 64.87 | 71.51 |
| 60 | 32.25 | 63.29 | 69.06 |
| 75 | 30.86 | 62.50 | 68.18 |
| 90 | 30.38 | 61.97 | 67.51 |
| 105 | 30.15 | 61.45 | 67.51 |
| 120 | 29.45 | 60.67 | 66.17 |

The data in Table 19 show that representative hydrophobically modified polymers are comparable to the benchmark for curl retention.

Example 18-21

Representative Hair Styling Formulations.

Representative Polymer in Hair Styling Formulations are shown in Examples 18-21.

Styling cream formulations prepared with or without a representative polymer of the invention and reference polymers are shown in Table 20.

TABLE 20

Styling Creams containing Representative Polymers

| Composition Ingredient | Weight % | Weight % |
|---|---|---|
| Water, Deionized | qs | qs |
| Polyquaternium-37/Propylene glycol/Dicaprylate Dicaprate and PPG-1 Trideceth-6[1], 50% | 4.00 | 4.00 |
| C16 Polymer | 1.00 | 0.00 |
| Water, Deionized | 10.00 | 10.00 |
| Polyvinypyrollidone[2] | 0.00 | 0.25 |
| Cyclopentasiloxane[3] | 1.00 | 1.00 |

[1]Salcare ® SC96, Ciba Specialty Chemicals, Highpoint, NC, USA.
[2]PVP-K30, International Specialties Products, Wayne, NJ, USA.
[3]Dow Corning ® 245 fluid, Dow Corning, Midland, MI, USA.

Example 19

Styling Mousse.

Styling mousse formulations prepared using hydrophobically modified polymers added creaminess and smoothed the hair. Representative formulations are shown in Table 21.

TABLE 21

Styling Mousse

| | Composition | |
|---|---|---|
| Ingredient | C-12 Polymer Weight % | C-8 Polymer Weight % |
| Water, Deionized | Qs | Qs |
| SD Alcohol 40 | 20.00 | 20.00 |
| C12 Polymer | 4.00 | 0.00 |
| C8 Polymer | 0.00 | 4.00 |
| Cetrimonium chloride | 1.00 | 1.00 |
| Preservative | Qs | Qs |
| Fragrance | Qs | Qs |

Example 20

Mineral Oil Gel

Mineral oil gels prepared using hydrophobically modified polymers provide extra conditioning and manageability in this gel. Representative formulations are shown in Table 22.

TABLE 22

Mineral Oil Gel

| | Composition | |
|---|---|---|
| Ingredient | C-12 Polymer Weight % | C-8 Polymer Weight % |
| Water, Deionized | qs | qs |
| C12 Polymer | 2.00 | 0.00 |
| C8 Polymer | 0.00 | 2.00 |
| Mineral Oil | 10.00 | 10.00 |
| Oleth-10 | 21.00 | 21.00 |
| PEG-25 Hydrogenated Castor Oil | 10.00 | 10.00 |
| Glycerol | 8.00 | 8.00 |
| Preservative | qs | qs |
| Fragrance | qs | qs |

Example 21

Leave-On or Rinse-Off Hair Taffy.

This formulation is tested on the hair for its ability to deep condition the hair. The formulation is allowed to dry on the hair and is then rinsed off to give a soft moisturized feel. The addition of the C12 or C8 polymer allows for silkier rinsing feel and added conditioning. Representative formulations are shown in Table 23

TABLE 23

Leave-on or rinse-off Hair Taffy

| Ingredient | Weight % | Weight % |
|---|---|---|
| Water | 91.04 | 90.50 |
| Polyacrylamide (and) C13-14 Isoparaffin (and) Laureth-7 | 4.00 | 4.00 |
| Cyclomethicone | 1.00 | 1.00 |
| PPG-10 Methyl Glucose Ether | 2.00 | 2.00 |
| C12 Polymer (5%) | 1.96 | 0.00 |
| C8 Polymer (8%) | 0.00 | 2.50 |
| Preservative | qs | qs |

Example 22

Evaluation of Spreading Ability of Various Surfactants and Polymers on Parafilm for Skin Care.

This study is performed as a quick screening method to approximate wetting behavior as described below.
1. 50 µl of a 0.2%, 1.0% solution or dispersion is pipetted onto flat sheets of 10 cm×10 cm Parafilm Wax.
2. After five minutes, the largest diameter of the droplet is measured. Triplicate samples are measured. The experiment is performed under ambient conditions (room temperature is 23° C.).
3. A spreading factor is calculated as the ratio of the test solution diameter to the distilled water diameter (0.6 cm or test average of three droplets).

The results are shown in Table 24.

TABLE 24

Relative Spreading of Various Surfactants under Ambient Conditions on a Parafilm Surface

| System | Diameter (cm) | Spreading Factor | Literature Surface Tension (dyne/cm) |
|---|---|---|---|
| Deionized Water | 0.58 | 1.00 | 72.8 |
| Cyclomethicone, neat | 3.37 | 5.81 | 20-35 |
| C8 Polymer, 0.2% | 0.58 | 1.00 | NA |
| C12 Polymer, 0.2% | 0.58 | 1.00 | NA |
| C16 Polymer, 0.2% | 0.58 | 1.00 | NA |
| C8 Polymer, 1.0% | 0.60 | 1.03 | NA |
| C12 Polymer, 1.0% | 0.63 | 1.05 | NA |
| C16 Polymer, 1.0% | 0.70 | 1.17 | NA |
| Sodium Lauryl Sulfate, 0.1% | 0.70 | 1.20 | 44.3 |

Formulations containing hydrophobically modified polymers, even with low hydrophobic substitution, are found to be surface active. Results show that the surface activity increases with alkyl chain length. C16 polymer is more surface active than C12 and C12 polymer self-associates more than the C8 polymer due to its foamy, viscous nature.

Examples 23-26

Representative Skin Care Formulations Containing Hydrophobically Modified Polymers.

Polymers of this invention can also be utilized for treating the skin. Without being bound by theory, polymers of this invention may form a protective film on the skin or nails. Skin care lotion formulations are shown in Examples 23-26.

In facial smoothing cream the addition of hydrophobically modified polymer creates very nice viscosity build that cannot be achieved with just salt alone. A representative formulation is shown in Table 25.

TABLE 25

Facial Smoothing Cream

| Ingredient | Weight % | Weight % |
|---|---|---|
| DI Water | 80.00 | 80.00 |
| Magnesium Aluminum Silicate[1] | 1.90 | 1.90 |
| Xanthan Gum[2] | 1.27 | 1.27 |
| Glycerol | 0.40 | 0.40 |
| Dimethicone Copolyol[3] | 0.10 | 0.10 |
| DMDM Hydantoin[4] | 0.20 | 0.20 |
| DI Water | 6.13 | 6.13 |
| C8 Polymer (5%) | 0.00 | 5.00 |
| DI Water | 10.00 | 5.00 |

[1]Veegum HV, R.T. Vanderbilt Company, Norwalk, CT USA.
[2]Keltrol CG-F, CP Kelco, Leatherhead, Surrey UK.
[3]Dow 193 Fluid, Dimethicone Copolyol, Dow Corning, Midland, MI USA.
[4]Glydant, Lonza, Fairlawn, NJ USA.

The Facial Smoothing Cream base [1.27% xanthan/1.9% magnesium aluminium silicate (MAS)] viscosity is significantly enhanced by the addition of 0.25% C8 polymer. The initial viscosity of the base without polymer is 6600 cps (5/20 30 sec at 23.5° C.). The viscosity upon addition of 0.25% C8 polymer is 16000 cps (6/20).

The hydrophobically modified polymers may be utilized as primary or secondary conditioning agents. They may be secondary for thickening, moisturizing, enhancing foam, forming films and perhaps stabilizing emulsion or dispersions.

Example 24

Bubble Bath.

Hydrophobically modified polymers give a soft and silky skin after feel in bubble bath formulations. A representative formulation is shown in Table 26

TABLE 26

Bubble Bath

| Ingredient | Weight % | Weight % |
|---|---|---|
| Water, Deionized | qs | qs |
| Ammonium Lauryl Sulfate, 29% | 35.00 | 35.00 |
| Cocamidopropyl Hydroxysultaine | 5.00 | 5.00 |
| Lauramide DEA | 4.00 | 4.00 |
| Disodium Laureth Sulfosuccinate | 8.00 | 8.00 |
| Hexylene Glycol | 2.00 | 2.00 |
| C12 Polymer | 3.00 | 0.00 |
| C8 Polymer | 0.00 | 3.00 |
| Citric Acid, 100% (s) | Qs pH 6.0 | Qs pH 6.0 |
| Sodium Chloride | 1.36 | 1.36 |
| Disodium EDTA | 0.10 | 0.10 |
| DMDM Hydantoin | 0.10 | 0.10 |
| Fragrance | Qs | Qs |

Example 25

Moisturizing Lotion.

Hydrophobically modified polymers give a soft and smooth after feel for the skin and contribute to emulsion spreadability of moisturizing lotion formulations. A representative formulation is shown in Table 27.

TABLE 27

| Moisturizing Lotion | | |
|---|---|---|
| Ingredient | Weight % | Weight % |
| Water | qs | Qs |
| Hydroxyethyl cellulose | 0.25 | 0.25 |
| Glycerol | 2.00 | 2.00 |
| Petrolatum | 2.00 | 2.00 |
| Mineral Oil | 4.00 | 4.00 |
| Cetyl Alcohol | 3.00 | 3.00 |
| Stearyl Alcohol | 2.00 | 2.00 |
| Polawax NF | 1.00 | 1.00 |
| Dimethicone 100cs | 0.50 | 0.50 |
| Acrylates/C10-30 Alkyl Acrylate Crosspolymer | 0.30 | 0.30 |
| Triethanolamine | 0.25 | 0.25 |
| C12 Polymer (5%) | 5.00 | 0.00 |
| C8 Polymer (8%) | 0.00 | 3.125 |
| Preservative | qs | qs |

Example 26

Evaluation of viscosity Enhancement of Liquid Hand Soap Formulations Containing Hydrophobically Modified Polymers.

A representative liquid hand soap formulation is shown in Table 28. Viscosity data is shown in Table 29.

TABLE 28

| Liquid Hand Soap Formulation | |
|---|---|
| Ingredient | Weight % |
| DI Water | qs |
| Sodium Lauryl Sulfate, 29% | 10.00 |
| Sodium Lauryl Ether Sulfate, 1 mole EO, 28% | 8.21 |
| Sodium Cocoyl Isethionate | 2.00 |
| C8 Polymer | 0.00 |
| C12 Polymer | 5.00 |
| Citric Acid, 100% (s) | 0.006 |
| Sodium Chloride | qs |
| Disodium EDTA | 0.10 |
| Kathon CG | 0.05 |
| DMDM Hydantoin | 0.10 |

TABLE 29

| Viscosity Measurement | |
|---|---|
| Sample | Viscosity 4/20 at 1.0% NaCl |
| Control Hand soap | 2540 |
| C12 Polymer | 3410 |
| Benchmark, Hydroxypropylmethyl cellulose | 1880 |

As shown in Table 29, the C12 hydrophobe polymer in combination with 1% sodium chloride provides higher viscosity than the control and benchmark hydroxypropyl methylcellulose material.

Example 27

Panel Combing Evaluation of Silicon Containing Hydrophobically Modified Polymers.

Hair tresses in duplicates are treated with two types of silicon modified polymer. The treated hair tresses are then rinsed under deionized water for 15 seconds. The treatment is repeated for another two times. The hair combing includes detangling and wet comb. The rating runs from 1 to 5. The higher number means hair is easier to detangle and comb. The following table summarizes the testing results from trained panelists. It indicates that two types of silicon modified polymer comb better than control.

TABLE 30

| Panel Combing for Silicon Modified Polymer | | |
|---|---|---|
| Name | Detangle | Combing Rate |
| Control | 2 | 2 |
| Polymer IX | 4.4 | 3.6 |
| Polymer X | 4.1 | 3.0 |

Example 28

Laundry Detergent Formulation.

Hydrophobiccally modified polymers show good compatibility with anionic surfactants and viscosity synergy. These advantages allow the representative polymers to be formulated in household cleaners and laundry and detergents. A representative laundry detergent formulation is shown in Table 31. The formulation is prepared by adding the ingredients in the order listed and dissolving each ingredient completely using moderate agitation. Color and fragrance additives may be incorporated as needed.

TABLE 31

| Value Performance Laundry Detergent | |
|---|---|
| Ingredient | % Wt |
| Water | qs |
| C12-Polymer | 2 |
| Tetra-sodium EDTA (38%) | 0.2 |
| $C_{12/14}$ Alkyl glycoside | 4.0 |
| Alkyl ethoxylate | 3.5 |
| Linear Alkylbenzene Sulfonic Acid, sodium | 6.5 |
| Monoethanolamine | 1.0 |

Although this invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

The invention claimed is:

1. A process for producing a cosmetically acceptable composition comprising preparing a mixture of an aqueous solution of a copolymer, an aqueous hydroxide solution, a sulfite solution, deionized water and a hydrophobic amine; stirring the mixture thoroughly, placing the mixture into a heating vessel and stirring consistently, pressurizing and venting the heating vessel, heating the heating vessel, cooling the heating vessel to ambient temperature, and collecting an aqueous solution of hydrophobically modified copolymer.

2. The process of claim 1 wherein the copolymer is a polyacrylamide.

3. The process of claim 1 wherein the sulfite solution is sodium metabisulfite.

4. The process of claim 1 wherein the pH during the process is about 5-11.

5. The process of claim 1 wherein the composition is heated to about 120-180° C.

6. The process of claim 1 wherein the composition is heated for 0.5 to 8.0 hours.

7. The process of claim 1 wherein the hydrophobically modified polymer is then diluted.

8. The process of claim 1 wherein the composition is treated with one or more preservatives.

9. The process of claim 2 wherein the polyacrylamide is cationic and composed of at least about 30 mole percent acrylamide.

10. The process of claim 1 wherein the copolymers contain monomers selected from diallyldimethylammonium chloride and methacrylamidopropyltrimethylammonium chloride.

11. The process of claim 9 wherein the cationic polyacrylamide is acrylamide/diallyldimethylammonium chloride copolymer.

12. The process of claim 9 wherein the cationic polyacrylamide is acrylamide/diallyldimethylammonium chloride/acrylic acid terpolymer.

13. The process of claim 1 wherein the hydrophobically modified polymer is combined with one or more cosmetically acceptable excipients.

14. The process of claim 13 wherein the cosmetically acceptable excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

15. The process of claim 13 wherein the cosmetically acceptable excipients are selected from the group consisting of shampoos, aftershaves, sunscreens, lotions, hand and body creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

16. The process of claim 1 wherein the hydrophobically modified polymer is combined with one or more of the following household cleaners and/or laundry detergents.

* * * * *